US008654319B2

United States Patent
Rao et al.

(10) Patent No.: US 8,654,319 B2
(45) Date of Patent: Feb. 18, 2014

(54) CHLOROPHYLL AND TURBIDITY SENSOR SYSTEM

(75) Inventors: Govind Rao, Ellicott City, MD (US);
Hung Lam, Baltimore, MD (US);
Yordan Kostov, Columbia, MD (US);
Leah Tolosa, Columbia, MD (US);
Xudong Ge, Ellicott City, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 249 days.

(21) Appl. No.: 13/142,284

(22) PCT Filed: Jan. 25, 2010

(86) PCT No.: PCT/US2010/021960
§ 371 (c)(1),
(2), (4) Date: Jun. 27, 2011

(87) PCT Pub. No.: WO2010/085736
PCT Pub. Date: Jul. 29, 2010

(65) Prior Publication Data
US 2011/0273705 A1    Nov. 10, 2011

Related U.S. Application Data

(60) Provisional application No. 61/146,804, filed on Jan. 23, 2009.

(51) Int. Cl.
*G01N 1/00* (2006.01)
(52) U.S. Cl.
USPC ............................... 356/73; 356/73.1; 356/72
(58) Field of Classification Search
USPC ......................................................... 356/73
See application file for complete search history.

(56) References Cited

U.S. PATENT DOCUMENTS

| | | | |
|---|---|---|---|
| 4,643,566 A | 2/1987 | Ohe et al. | |
| 5,304,492 A | 4/1994 | Klinkhammer | |
| 5,325,169 A | 6/1994 | Nakamoto et al. | |
| 6,445,856 B1* | 9/2002 | Yang | 385/48 |
| 2004/0017569 A1* | 1/2004 | Payne | 356/436 |
| 2004/0090168 A1 | 5/2004 | Kumar et al. | |
| 2005/0021244 A1 | 1/2005 | Nicoli et al. | |
| 2005/0041141 A1* | 2/2005 | Stephens | 348/370 |
| 2005/0104008 A1 | 5/2005 | Oostman et al. | |
| 2005/0142662 A1 | 6/2005 | Bonne | |
| 2006/0208171 A1 | 9/2006 | Holland | |

(Continued)

OTHER PUBLICATIONS

G.H. Krause et al.,"Chlorophyll Fluorescence and Photosynthesis: The Basics", Annu. Rev. Plant Physiol. Plant Mol. Bioi., vol. 42, Jan. 1, 1991, pp. 313-349, XP55026757, Annual Reviews Inc., Palo Alto, CA 94306.

(Continued)

*Primary Examiner* — Tarifur Chowdhury
*Assistant Examiner* — Omar Nixon
(74) *Attorney, Agent, or Firm* — Rene A. Vazquez, Esq.

(57) ABSTRACT

A low cost sensing system that can measure both chlorophyll concentration and turbidity is provided. The system is an optical system that utilizes at least three light sensors for measuring side-scattered and forward scattered light, as well as fluorescence. The system is able to take optical density measurements, steady state fluorescence measurements and maximum fluorescence measurements, and can be configured for wireless control and data transmission. The system may also be housed in one or more fluidtight housings so as to make it submersible.

25 Claims, 4 Drawing Sheets

(56) References Cited

U.S. PATENT DOCUMENTS

2006/0228256 A1  10/2006  McDevitt et al.
2007/0116601 A1   5/2007  Patton
2007/0149863 A1*  6/2007  Padmanabhan et al. ...... 600/309
2007/0216898 A1*  9/2007  Gardner, Jr. .................. 356/301
2008/0024758 A1   1/2008  Tabata
2008/0064053 A1   3/2008  Walmsley et al.
2008/0274494 A1* 11/2008  Kertz ............................. 435/29

OTHER PUBLICATIONS

YSI Environmental: "In Vivo Measurement of Chlorophyll and the YSI 6025 Wiped Chlorophyll Sensor", YSI Environmental White Paper, Jan. 1, 2006, pp. 1-4, XP55026758, Yellow Springs, Ohio 45387.

International Search Report, PCT/US2010/021960, mailed Apr. 29, 2010.

* cited by examiner

CHLOROPHYLL AND TURBIDITY SENSOR SYSTEM

This application claims priority to U.S. Provisional Application Ser. No. 61/146,804, filed Jan. 23, 2009, whose entire disclosure is incorporated herein by reference.

BACKGROUND OF THE INVENTION

1. Field of the Invention

The present invention relates to monitoring of environmental parameters and, more particularly, to combined chlorophyll and turbidity sensor system.

2. Background of the Related Art

Real time and in situ measurement of chlorophyll is extremely important for understanding the status of an ecosystem. The chlorophyll concentration is the primary indicator for the biomass-productivity of a system. The increase of nutrients in an aquatic system boosts the production of biomass. However, the productivity rate is shown to be dependent, not only on the nutrients concentration, but also on the water turbidity, as discussed in E. G. DeGroodt and V. N. de Jonge; Effects of changes in turbidity and phosphate influx on the ecosystem of the Ems estuary as obtained by a computer simulation model; Hydrobiologia; Volume 195, Number 1/April, 1990, which is incorporated by reference herein in its entirety.

The more suspended and dissolved substances in the water, the more sun light is absorbed by them, leaving little to the photosynthetic plankton and plants. Drastic changes in either chlorophyll or turbidity endanger the equilibrium of the ecosystem. In order to observe the chlorophyll concentration and the turbidity of an aquatic system, such as lakes, rivers or maritime locations, many probes have to be employed so that a large area can be covered. Hence, the probes must be reliable and low cost.

SUMMARY OF THE INVENTION

An object of the invention is to solve at least the above problems and/or disadvantages and to provide at least the advantages described hereinafter.

Therefore, an object of the present invention is to provide a system for real time, in-situ measurement of chlorophyll and turbidity.

To achieve at least the above objects, in whole or in part, there is provided a sensor probe for obtaining measurements in a liquid, comprising a housing with a shape that defines a flow-through area that is open to the environment and through which a liquid can flow through, a light source, and at least three light sensors, wherein the light source and the at least three light sensors are positioned in the housing around the flow-through cell such that light from the light source propagates into the flow-through area, at least some light side-scattered by material in the flow through area is collected by at least two of the light sensors, and at least some light that is not absorbed or side-scattered in the flow-through area is collected by a third of the at least three light sensors.

To achieve at least the above objects, in whole or in part, there is also provided a sensor system, comprising a sensor probe, wherein the sensor probe comprises a housing with a shape that defines a flow-through area that is open to the environment and through which a liquid can flow through, a light source, and at least three light sensors, wherein the light source and the at least three light sensors are positioned in the housing around the flow-through cell such that light from the light source propagates into the flow-through area, at least some light scattered by material in the flow through area is collected by at least two of the light sensors, and light that is not absorbed or side-scattered in the flow-through area is collected by a third of the at least three light sensors and a control system attached to and in electrical communication with the submersible probe.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

The description below cites numerous technical references, all of which are incorporated by reference herein in their entirety.

The present invention provides a low cost sensing system that can measure both chlorophyll concentration and turbidity. The present system is useful for monitoring the health of coastal areas and ecosystems. Alternatively, the present system may be utilized for measuring both chlorophyll concentration and turbidity in bioprocessing systems such as bioreactors, preferably bioreactors used for the cultivation of plant cells, such as algae.

Figure 1A:
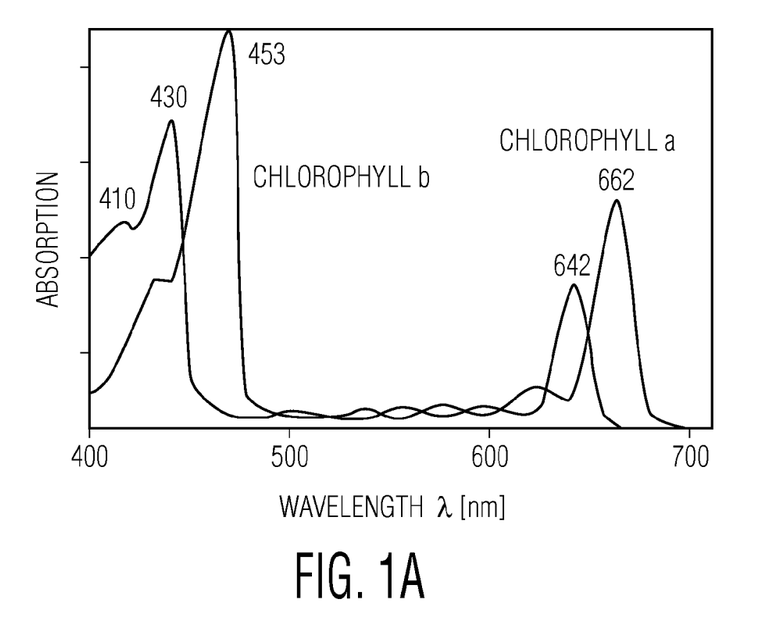
FIGS. 1A and 1B are plots showing the absorption and fluorescence spectra of chlorophyll A.
Figure 1B:
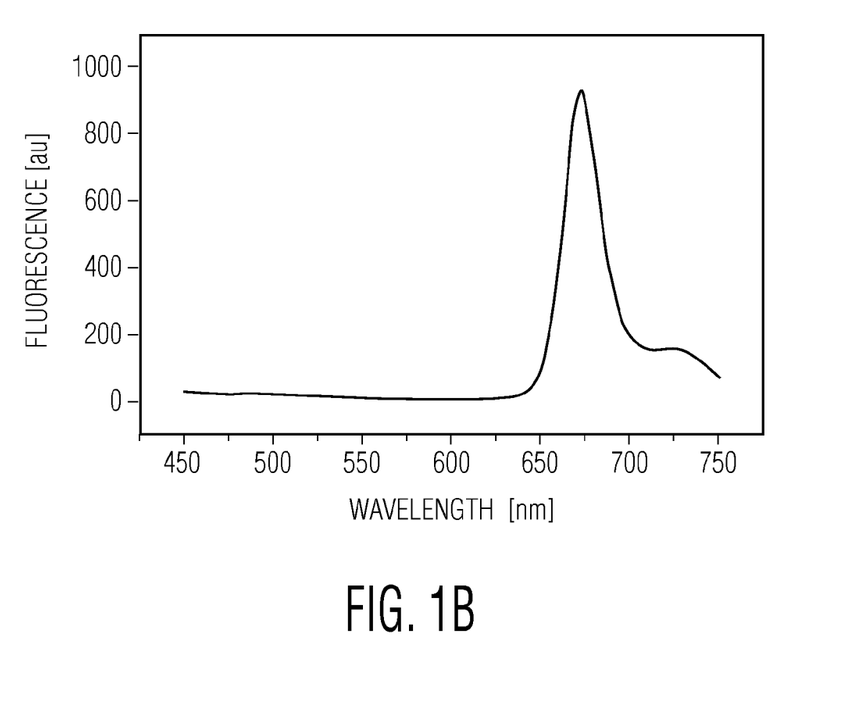

Generally, there are two methods for measuring chlorophyll, both of which are based on the absorbance and fluorescence of chlorophyll A. As shown in FIGS. 1A and 1B, the concentration of Chlorophyll A can be measured either by its absorption peaks at 430 and 680 nm (662 nm in acetone solution) or its fluorescence at 683 nm (excitation at 470 nm) (Krause G H, Weis E.; Chlorophyll fluorescence and photosynthesis, the basics; Annual Review of plant physiology and plant molecular biology; 1991, 42, 313-349).

Under controlled laboratory conditions both absorption and fluorescence can be used with proper accuracy. Under field conditions or bioprocessing conditions in a bioreactor however, a probe has to cope with changing conditions, such as changes in ambient scattered light and temperature, which effect the optical properties of the sample. Moreover, the presence of other particles that absorb light, such as minerals and dead organic matter, also has a significant impact on both fluorescence and absorption. Thus the actual concentration may not be obtained by measuring just the fluorescence or just the turbidity.

In addition, only approximately 3-5% of the absorbed light energy is dissipated as fluorescence (Bilger H. W., Schreiber U. and Lange O. L.; Determination of leaf heat resistance, comparative chlorophyll fluorescence changes and tissue necrosis method; Oekologia, 1986, 36, 256-262). The fluorescence peak for chlorophyll A is at 683 nm. Since chlorophyll A also shows an absorption band at the same wavelength region, the fluorescence is further reduced by the inner filter effect (Ahmed, S., A. Gilerson, A. Gill, B. M. Gross, F, Moshary, J. Zhou; Fluorescence and Elastic Scattering from Algae in Seawater Using Polarization Discrimination. Opt. Com., 2004, 235, 23-30). Due to all these effects, the fluorescence intensity is very low.

Unlike commercially available chlorophyll probes, which only measure fluorescence without considering the factors discussed above, the present invention utilizes the following:
(1) Maximizing the harvest of fluorescence;
(2) Measuring the turbidity of the overall disturbing substances;
(3) Measuring the absorption caused by the chlorophyll;
(4) Compensating for temperature effects; and
(5) Applying an algorithm to calculate the actual fluorescence.

In addition, with the present system, fluorescence quantum yield can be measured, the efficiency of photochemical quenching can be derived and particle size can be estimated.

Figure 2:
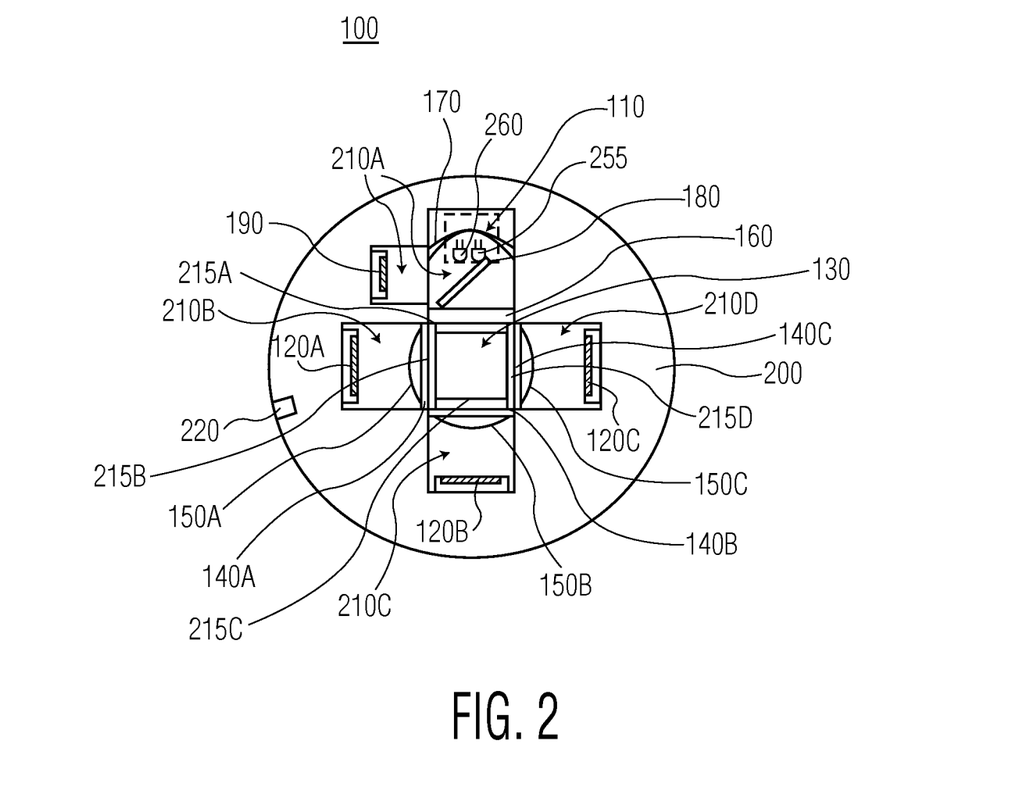
FIG. 2 is a schematic cross-sectional top view of a combined chlorophyll and turbidity sensing probe, in accordance with one preferred embodiment of the present invention.

FIG. 2 is a schematic cross-sectional top view of a combined chlorophyll and turbidity sensing probe 100, in accordance with one preferred embodiment of the present invention. It includes a light source 110 that is preferably capable of outputting light at selectable spectra, preferably selectable spectra with emission maxima at approximately 660 nm, 470 nm and 525 nm.

Three sensitive photodiodes 120A, 120B and 120C function as the combined detector for the light signal. Three photodiodes are used so as to maximize the amount of signal light captured. The light source 110 and the detectors 120A-120C are preferably housed in a disc-shaped housing 200, suitably formed from aluminum or plastics, the latter being preferably sterilizable prior to use, and positioned so as to form a "cross" configuration whose center is free space with a predefined volume that functions as a flow through cell 130.

Between the flow through cell 130 and the photodiodes 120A-120C are optical filters 140A-140C and lenses 150A-150C which filter and focus the signal light onto the photodiodes 120A-120C. A collimating lens 160 and a parabolic mirror 170 are configured to substantially collimate the light from the light source 110 so as to illuminate substantially all of the flow through cell 130 without directing light from the light source 110 directly into the two side photodiodes 120A and 120C. The collimating lens is preferably an achromatic lens, so as to reduce chromatic aberration. The optical filters 140A-140C are each preferably long pass filters with a cutoff of approximately 500 nm. A temperature sensor 220, preferably a thermistor, is preferably included and positioned on the housing 200 so as to be in contact with the environment outside the housing 200 (e.g., in contact with water or the medium in a bioreactor). The temperature sensor 220 is used to monitor environmental temperature for compensating for any temperature effects.

A beam splitter 180 is positioned between the light source 110 and the collimating lens 160 for reflecting a portion of the light from the light source 110 towards reference photodiode 190. The beam splitter 180 is preferably configured to reflect at preferably no more than approximately 10% of the light towards the reference photodiode 190. The remaining light that is not reflected or absorbed by the beam splitter 180 is transmitted to the collimating lens 160.

The housing 200 includes cavities 210A-210D for accommodating the photodiodes 120A-120C, light source 110, parabolic mirror 170, beam splitter 180, collimating lens 160, filters 140A-140C and lenses 150A-150C. The filters 140A-140C act as the outside walls of the cavities 210B-210D, respectively. Collimating lens 160 acts as the outside wall for cavity 210A. The cavities 210B-210D are preferably fluidtight (for example, watertight) cavities so that the probe 100 is submersible. This is preferably accomplished by attaching the optical windows 215A-215D so as to form a fluidtight seal, thereby keeping water out of the cavities 210A-210D. The optical windows 215A-215D are preferably coated with a perfluorinated sol gel coating so as to inhibit biofouling, should the probe be submersed in a water or in a medium of a bioreactor for an extended period of time.

The light source 110 preferably consists of an ultra bright blue LED 255, preferably with an output power of at least 1 W and an output spectra having an emission maximum at approximately 470 nm, and an RGB-LED 260. The RGB LEDs are commercially available and can emit red, green and/or blue light. The RGB LED 260 is preferably chosen so that it can emit red light with an output spectrum having an emission maximum at approximately 660 nm and an output power of at least 100 mW, green light with an output spectrum having an emission maximum at approximately 525 nm and an output power of at least 100 mW, and a blue light with an output spectrum having an emission maximum at approximately 470 nm and an output power of at least 100 mW. Although LEDs are preferably used as the light source 110, other types of light sources, such as laser diodes, may be also be used.

The probe 100 preferably has two modes of operation: (1) an optical density (OD) measurement mode; and (2) a fluorescence measurement mode. The fluorescence measurement mode preferably has two sub modes of operation: (1) a steady state fluorescence mode $F_t$; and (2) a maximum fluorescence mode $F_{max}$. These modes of operation will be discussed in more detail below.

OD Measurement Mode

Sea water, especially near the coast, contains not only algae, but also mineral particles, dead organic materials, tannic agents etc., while culture media in bioreactors may accumulate cell debris or other biomolecule aggregates as a result of longer cultivation duration. Thus, a simple OD measurement would only give the absorbance of all these compositions. In order to obtain the absorbance of only chlorophyll A, a differential measurement has to be carried out.

As shown in FIGS. 1A and 1B, chlorophyll A absorbs blue and red light, but green light is not absorbed. The absorbance of chlorophyll A is obtained in two steps. First red light (preferably an emission maximum at approximately 660 nm) is used, which is absorbed by all materials. Photodiodes 120A and 120C measure the side-scattered light while photodiode 120B detects the forward-scattered light. The scattered light measured is reduced by the amount of light that has been absorbed. The total output light intensity of the light source 110 is monitored by the reference photodiode 190. This is important in order to quantify the absorbance, which is some fraction of the total light intensity. The reference photodiode monitors keeps track of any fluctuation in the output light intensity of the light source 110.

In a second step, green light (preferably an emission maximum at approximately 525 nm) is transmitted, which is not absorbed by chlorophyll A. Hence, the intensity of the scattered light is higher by an amount proportional to the reduced absorbance. By comparing the absorbance from the red and green light measurements, the absorbance from chlorophyll A can be determined as follows:

$$Abs(red) = Abs(chlorophyll\ A) + Abs(contaminants) \quad (1)$$

$$Abs(green) = Abs(contaminants) \quad (2)$$

$$Abs(chlorophyll\ A) = Abs(red) - a^*Abs(green) \quad (3)$$

where the coefficient "a" is a compensating factor that compensates for the difference in photodiode light sensitivity at different wavelengths. For example, silicon-based photodiodes are more sensitive at longer wavelengths. Thus, the absorbance of chlorophyll A may be determined by subtracting the light scattering values obtained with green light (as adjusted by compensating factor "a") from the light scattering values obtained with red light.

A further use of the scattered light measurements is the estimation of the size of the particles that are causing the scattering. According to Fraunhofer diffraction law, for particles that are larger than the wavelength of light, the light scatters from the edge of the particle at an angle that is dependent on the size of the particle. Larger particles scatter light at relatively smaller angles than those from light scattered from smaller particles. By comparing the intensity of forward-scattered light with the intensity of the side-scattered light, the average size of the particles in the sample can be estimated (Sloan C. K. and Arrington C. H., Jr., papers presented at the 125$^{th}$ National Meeting, American Chemical Society, Kansas City, Mo., April 1954; C. K. Sloan, J. Phys. Chem. 59, 834 (1955)).

Fluorescence Measurement Mode

For the excitation of chlorophyll A, blue light from the light source 110 is used with a maximum emission at preferably approximately 470 nm. The steady state fluorescence of chlorophyll A is captured by all three photodiodes 120A-120C. The measured steady state fluorescence is then corrected by taking the partial loss of fluorescence through absorption by contaminants into consideration. The long pass optical filters 150A-150C effectively block the blue excitation light, while transmitting the red/orange fluorescence light.

For the measurement of the maximum fluorescence the "light doubling" technique is preferably used (Bradbury and Baker; Analysis of the slow phases of the in vivo chlorophyll fluorescence induction curve. Changes in the redox state of the photosystem II electron acceptors and fluorescence emission from photosystem I and II; Biochimica and Biophysica, 1991, 635, 542-551). The ultra bright 1 W blue LED is preferable used as the light source, which makes it possible to create a short and intensive light pulse. The short and intensive light pulse deactivates the photosystem II so that the absorbed light energy is not used for photochemical processes, but mainly reemitted as fluorescence. The blue light pulse used to achieve this is suitably one with a pulse length of 1.3 seconds and a peak power of 100 mW/cm$^2$. By measuring both the steady state fluorescence and the maximum fluorescence, the photochemical efficiency (Φ) of the autotrophic cells' photosystems may also be calculated as follows:

$$\Phi = \frac{F_{max} - F_t}{F_{max}} \quad (4)$$

Electronics

Figure 3:
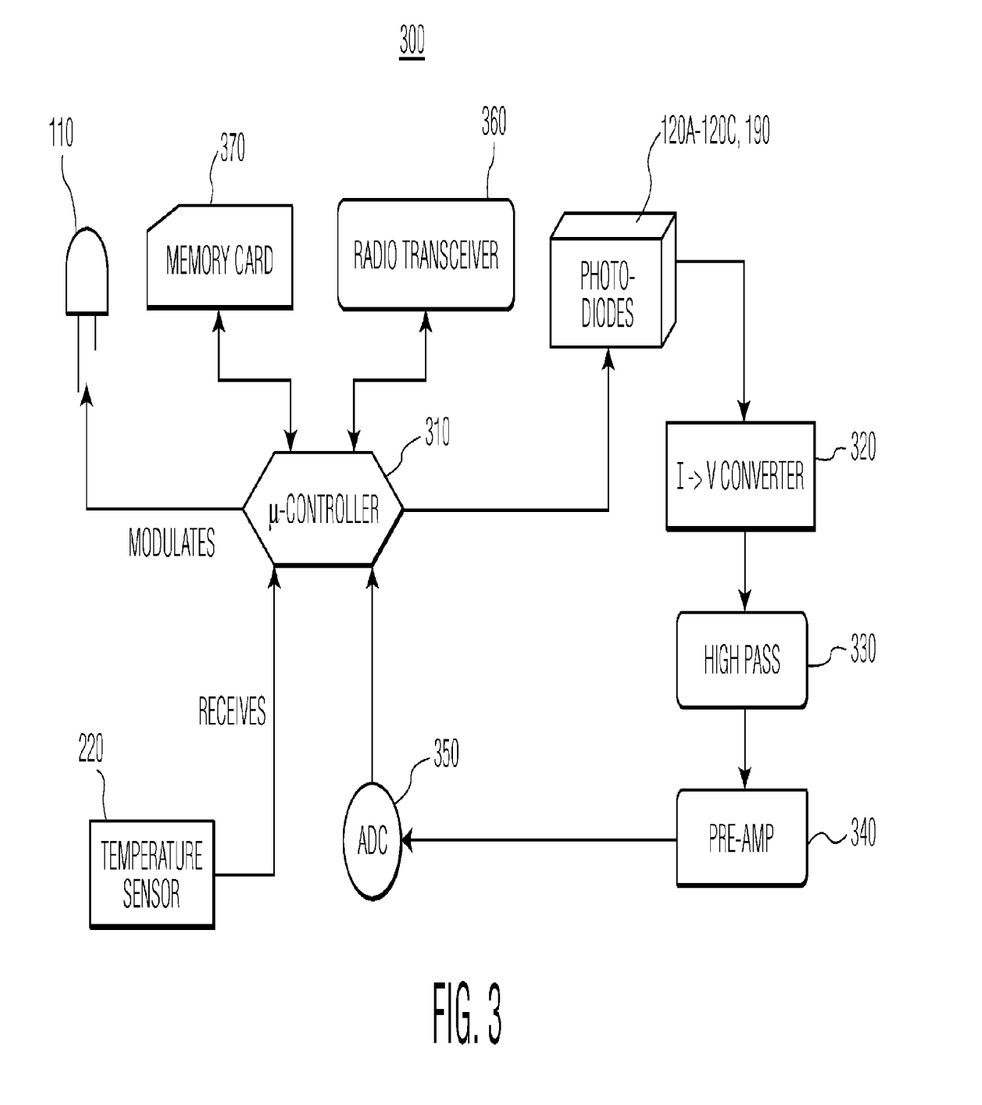
FIG. 3 is a schematic diagram of electronics that are preferably used with the chlorophyll and turbidity sensing probe of FIG. 2, in accordance with one preferred embodiment of the present invention.

FIG. 3 is a schematic diagram of a control system 300 that is preferably used with the chlorophyll and turbidity sensing probe 100. The control system 300 include a microcontroller 310 that provides overall measurement and control functions, a current-to-voltage converter 320, a high pass filter 330 that is adapted to cut off any signal that originates from ambient light, an amplifier 340, and an analog-to-digital converter (ADC) 350.

In operation, the microcontroller controls the operation of the photodiodes 120A-120C and 190 and the light source 110. The photodiodes 120A-120C and 190 output a current in proportion to the amount of light hitting them. The current is converted to a voltage by the current-to-voltage converter 320. The voltage signal is filtered by high pass filter 330 and amplified by amplifier 340. The ADC 350 converts the analog voltage to a digital signal that is then input into the microcontroller 310 for analysis. If a temperature sensor 220 is used, the output of the temperature sensor is also sent to the microcontroller for analysis. The microcontroller 310 may optionally communicate (send data and receive commands) with a remote user wirelessly by using a radio transceiver 360.

The light source 110 is preferably modulated by the microcontroller 310 and the measured signal is preferably further processed by the microcontroller 310 using a digital lock-in algorithm which, in conjunction with the high pass filter 330, reduces the noise and unwanted background signal caused by ambient light. A digital lock-in algorithm is much more efficient than an analog counterpart, which requires extra electronic components that add noise to the circuit increases the cost.

The microcontroller 310 preferably saves the processed data in memory, suitably a memory card 370 (e.g., an SD card), to ensure that the data is not lost even if a power blackout occurs. The electronics in the control system 300 are preferably designed for low power consumption by using low power consuming electronics and energy management algorithms.

As discussed above, the microcontroller 310 preferably communicates with a user wirelessly, preferably via radio transmission, RFID (radio frequency identification) or bluetooth technology. Measurement data may be sent to a user wirelessly and the user can preferably stop or change the measurement option by transmitting commands over radio to the microcontroller 310. All electronic components are preferably robust so as to withstand harsh conditions.

Figure 4:
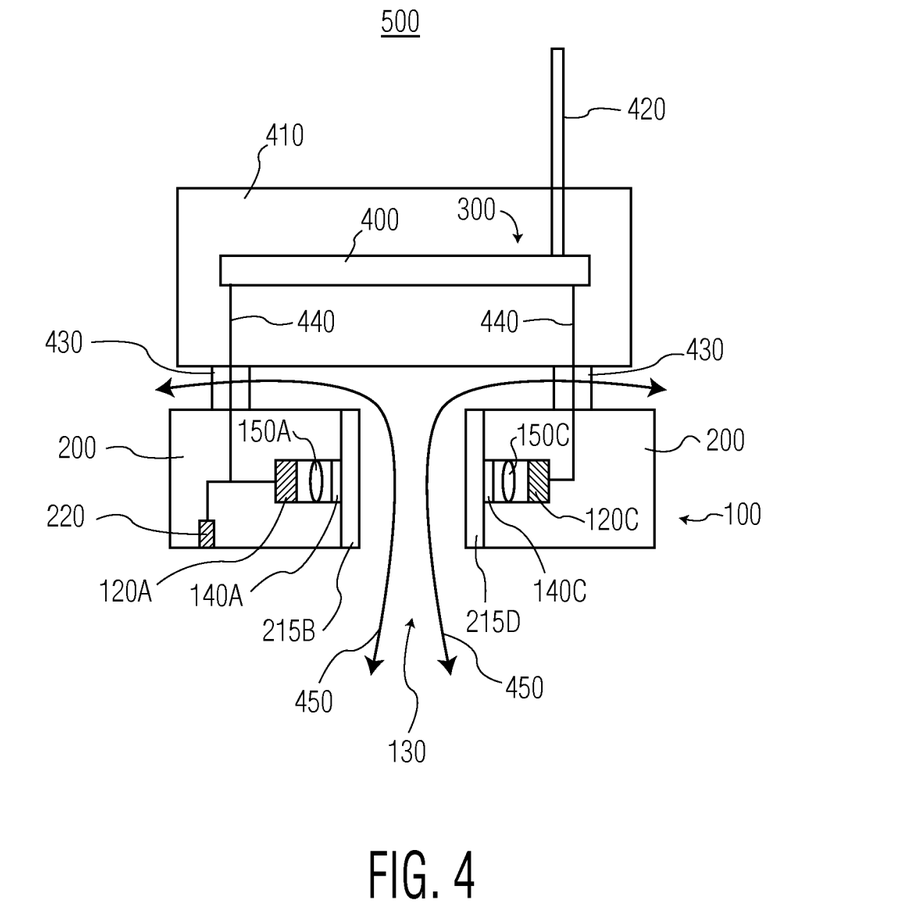
FIG. 4 is a side cross-sectional schematic view of a chlorophyll and turbidity sensing system, in accordance with one preferred embodiment of the present invention.

FIG. 4 is a side cross-sectional schematic view of one example of how the control system 300 and the chlorophyll and turbidity sensing probe 100 may be connected together to form a complete chlorophyll and turbidity sensing system 500, in accordance with one embodiment of the present invention. The microcontroller 310, current-to-voltage converter 320, high pass filter 330, amplifier 340 and the ADC 350 are all preferably installed on circuit board 400. The circuit board 400 is preferably housed in a housing 410, preferably a fluidtight, preferably liquidtight housing so that the system 500 may be submersed in water or other liquid. An antenna 420 is preferably in electrical communication with the electronics board 400 for wireless communications, as described above.

Housing 410 is preferably connected to housing 200 with hollow connectors 430, which allow for the passage of the electrical wires 440 that connect the circuit board to the light source, photodiodes and temperature sensor. In operation, water 450 flows through the cell 130 as shown. Alternatively, a medium of a bioreactor may be directed through the cell 130, preferably by way of an external circulation loop connecting the cell 130 with the bioreactor.

To protect the system 500 from bio fouling, should the system be submersed for an extended period of time, the outer surfaces of the housings 200 and 400 are preferably coated with a double layer of copper containing paint and light stimulated nitric oxide polymer, which is proven to inhibit settlement of micro-organisms. Alternatively, for bioprocessing applications, the housings 200 and 400 can be coated with biocompatible or plastics polymers having antifouling properties. The plastics polymer coating is preferably sterilizable prior to use of the system.

The chlorophyll and turbidity sensing system 500 can be enclosed in a buoy as a standalone system floating on the water or bioreactor medium for measuring the surface chlorophyll concentration, or can be tied to a cable and submerged manually by a user to a desired water depth or level in the bioreactor.

The foregoing embodiments and advantages are merely exemplary, and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. Various changes may be made without departing from the spirit and scope of the invention, as defined in the following claims. For example, although the present sensor system has been described in connection with a combined chlorophyll and turbidity sensing system, it can be adapted for the optical sensing of other environmental parameters by choosing the appropriate light source and light sensors.

What is claimed is:

1. A sensor probe, comprising:
   a housing with a shape that defines a flow-through area that is open to the environment and through which a liquid can flow through;
   a light source; and
   at least three light sensors;
   wherein the light source and the at least three light sensors are positioned in the housing around the flow-through cell such that light from the light source propagates into the flow-through area, at least some light side-scattered by material in the flow-through area is collected by at least two of the light sensors, and at least some light that is not absorbed or side-scattered in the flow-through area is collected by a third of the at least three light sensors.

2. The sensor probe of claim 1, wherein the light source and the at least three light sensors are each positioned in separate respective cavities within the housing.

3. The sensor probe of claim 2, wherein the cavities each comprise an optical window, adjacent to and that partially defines the flow-through area, that transmits light from the light source.

4. The sensor probe of claim 3, wherein each of the at least three light sensors comprise:
   a photodiode;
   an optical filter positioned between a respective optical window and the photodiode; and
   a lens positioned between the photodiode and the respective optical window for focusing light onto the photodiode.

5. The sensor probe of claim 4, further comprising a reference photodiode positioned to monitor a portion of the light from the light source prior to entering the flow-through area.

6. The sensor probe of claim 5, further comprising a beam splitter positioned between the light source and a respective optical window for reflecting a portion of the light from the light source towards the reference photodiode.

7. The sensor probe of claim 3, further comprising a collimating lens positioned between the light source and a respective optical window for substantially collimating the light from the light source prior to the light entering the flow-through area.

8. The sensor probe of claim 4, wherein the light source comprises an RGB LED, and a blue LED with an output power of at least 1 W.

9. The sensor probe of claim 8, wherein the RGB LED comprises:
   a red LED with an output spectrum having an emission maximum at approximately 660 nm;
   a green LED with an output spectrum having an emission maximum at approximately 525 nm; and
   a blue LED with an output spectrum having an emission maximum at approximately 470 nm.

10. The sensor probe of claim 9, wherein each of the optical filters comprise long pass filters with a cutoff wavelength of approximately 500 nm.

11. The sensor probe of claim 2, wherein the respective cavities comprise fluidtight cavities such that the sensor probe is submersible.

12. A system for monitoring chlorophyll concentration and/or turbidity in a bioreactor using the sensor probe as in any of claims 1-11.

13. A sensor system, comprising:
   a sensor probe, wherein the sensor probe comprises,
      a housing with a shape that defines a flow-through area that is open to the environment and through which a liquid can flow through,
      a light source, and
      at least three light sensors,
      wherein the light source and the at least three light sensors are positioned in the housing around the flow-through cell such that light from the light source propagates into the flow-through area, at least some light scattered by material in the flow through area is collected by at least two of the light sensors, and light that is not absorbed or scattered in the flow-through area is collected by a third of the at least three light sensors; and
   a control system attached to and in electrical communication with the probe.

14. The sensor system of claim 13, wherein the light source comprises an RGB LED, and a blue LED with an output power of at least 1 W.

15. The sensor system of claim 14, wherein the RGB LED comprises:
   a red LED with an output spectrum having an emission maximum at approximately 660 nm;
   a green LED with an output spectrum having an emission maximum at approximately 525 nm; and
   a blue LED with an output spectrum having an emission maximum at approximately 470 nm.

16. The sensor system of claim 15, wherein the control system is programmed to operate the sensor probe in at least an optical density measurement mode, a steady state fluorescence measurement mode and a maximum fluorescence measurement mode.

17. The sensor system of claim 16, wherein, in the optical density measurement mode, the control system:
   controls the light source so that the light source emits red light with an emission maximum at approximately 660 nm;
   determines the amount of side-scattered and forward-scattered red light using the at least three light sensors;
   controls the light source so that the light source emits green light with an emission maximum at approximately 525 nm;

determines the amount of side-scattered and forward-scattered green light using the at least three light sensors; and
determines an absorbance of chlorophyll based on the red and green scattered light measurements.

18. The sensor system of claim 16, wherein, in the steady state fluorescence measurement mode, the control system:
controls the light source so that the light source emits pulsed blue light with an emission maximum at approximately 470 nm; and
determines the amount of fluorescence induced by the pulsed blue light using the at least three light sensors.

19. The sensor system of claim 16, wherein, in the maximum fluorescence measurement mode, the control system:
controls the light source so that the light source emits pulsed blue light with an emission maximum at approximately 470 nm and with a peak power sufficient to deactivate the photosystem II of chlorophyll; and
determines the amount of fluorescence induced by the pulsed blue light using the at least three light sensors.

20. The system of claim 13, wherein each of the at least three light sensors comprise a photodiode, and wherein the control system comprises:
a current-to-voltage converter in electrical communication with the photodiodes for converting an electrical current signal from the photodiode to a voltage;
a high pass electrical filter that for receiving and filtering a voltage signal from the current-to-voltage converter;
an amplifier for amplifying a filtered voltage signal from the high pass filter;
an analog-to-digital converter for receiving an amplified signal from the amplifier and converting the amplified signal to a digital signal; and
a microcontroller in electrical communication with the light source, photodiodes, and analog-to-digital converter.

21. The system of claim 20, wherein the control system further comprises a radio transceiver in electrical communication with the microcontroller for wirelessly transmitting data and wirelessly receiving control signals.

22. The system of claim 13, wherein the sensor probe further comprises a temperature sensor positioned to measure environmental temperature.

23. The system of claim 13, wherein the light source and the at least three light sensors are each positioned in separate respective cavities within the housing.

24. The system of claim 23, wherein the respective cavities comprise fluidtight cavities and the control system is housed in a fluidtight housing such that the system is submersible.

25. A system for monitoring chlorophyll concentration and/or turbidity in a bioreactor using the sensor system as in any of claims 13-24.

* * * * *